United States Patent [19]
Busch et al.

[11] Patent Number: 5,656,743
[45] Date of Patent: Aug. 12, 1997

[54] OLIGONUCLEOTIDE MODULATION OF CELL GROWTH

[75] Inventors: Harris Busch, Houston, Tex.; Clarence Frank Bennett, Carlsbad, Calif.; Laszlo Perlaky, Houston, Tex.; Yasuo Saijo, Sendai, Japan; Rose K. Busch, Houston, Tex.

[73] Assignees: Baylor College of Medicine, Houston, Tex.; ISIS Pharmaceuticals, Inc., Carlsbad, Calif.

[21] Appl. No.: 290,936

[22] Filed: Nov. 18, 1994

Related U.S. Application Data

[63] Continuation-in-part of PCT/US93/00754, Jan. 27, 1993, and a continuation-in-part of Ser. No. 841,660, Feb. 19, 1992, abandoned.

[51] Int. Cl.$^6$ .......................... C07H 21/00; A61K 48/00
[52] U.S. Cl. .......................................................... 536/24.5
[58] Field of Search ............................... 514/44; 536/24.5

[56] References Cited

U.S. PATENT DOCUMENTS 5,098,890  3/1992  Gewirtz et al. ........................ 514/44

FOREIGN PATENT DOCUMENTS

WO93/15743  8/1993  WIPO.

OTHER PUBLICATIONS

Milligan et al, J. Medicinal Chemistry, 36(14):1923–1937 (1993).
Westermann et al, Biomed. Biochem. Acta, 48(1):85–93 (1989).
Bennett, Science, 271:434 (1996).
Bottenu et al. Nucleotide Sequence of the Gene for the b Subunit of Human Factor XIII *Biochemistry* 1900 29:11195–11209.
Mirabelli et al. In vitro and in vivo pharmacologic activities of antisense oligonucleotides *Anti–Cancer Drug Design* 1991 6:647–661.
Chiang et al. Antisense Oligonucleotides Inhibit Intercellular Adhesion Molecule 1 Expression by Two Distinct Mechanisms *Journ. of Biol. Chem.* 1991 206:18162–18171.
Perlaky et al. Growth Inhibition of Human Tumor Cell Lines by Antisense Oligonucleotides Designed to Inhibit p120 Expression *Anti–Cancer Drug Design* 1993 8:3–14.
Perlaky et al. Nucleolar and nuclear aberrations in human lox tumor cells following treatment with p120 antisense oligonucleotide *Cancer Letters* 1993 74:125–135.
Saijo et al. Cellular Pharmacology of p120 Antisense Oligodeoxynucleotide Phosphorothioate *Oncology Research* 1993 5:283–291.
Reed et al., Cancer Research, 50:6565–6570 (1990).
Anfossi et al., Proc. Natl. Acad. Sci USA, 86:3379–3383 (1989).
Fonagy et al., Proc. Am. Assoc. Cancer Res. Annu. Meet., 32:277 (1991).
Uhlmann et al., Chemical Reviews, 90(4):544–584 (1990).
Fonagy et al., Cancer Research, 54:1859–1864 (1994).

Fonagy et al., Cancer Research, 52:5250–5256 (1992).
Valdez et al., Cancer Research, 52:5681–5687 (1992).
Perlaky et al., Cancer Research, 52:428–436 (1992).
Tsujino et al., J. Biol. Chem., 264(26):15334–15337 (1989).
Busch H. et al., "Nucleolar Protein P120 and Its Targeting for Cancer Chemotherapy" Boll Soc. It Biol Sper. 67: 739–750 (1991).
Busch et al., "The Final Common Pathway of Cancer: Presidential Address" *Cancer Res.*, 50: 4830–4838 (1990).
Calabretta, "Inhibition of Protooncogene Expression by Antisense Oligodeoxynucleotides: Biological and Therapeutic Implications" Cancer Res 51: 4505–4510 (1991).
Fonagy et al., "Cloning of the cDNA and Sequence of the Human Proliferating–Cell Nucleolar Protein P120" *Cancer Commun.* 1: 243–245 (1989).
Freeman and Bondada, "Inhibition of Cell Proliferation by Microinjection of Antibodies to Nucleolar Antigen p120" *Proc. of the Am. Assoc. Cancer Res.* 31: 261 (1990) (Abstract 1547).
Freeman et al., "Identification and Characterization of a Human Proliferation–Associated Nucleolar Antigen with a Molecular Weight of 120,000 Expressed in Early $G_1$" *Cancer Res.* 48: 1244–1251 (1988).
Freeman et al., "Prognostic Significance of Proliferation Associated Nucleolar Antigen P120 in Human Breast Carcinoma" *Cancer Res.* 51: 1973–1978 (1991).
Larson et al., "Genomic Structure of the Human Proliferating Cell Nucleolar Protein P120" *Cancer Commun.* 2: 63–71 (1990).
Ochs et al., "Intranucleolar Localization of Human Proliferating Cell Nucleolar Antigen p120" *Cancer Res.* 48: 6523–6529 (1988).
Rothenberg et al., "Oligodeoxynucleotides as Anti–Sense Inhibitors of Gene Expression: Therapeutic Implications" *J. Natl. Cancer Inst.* 81: 1539–1544 (1989).
Stein and Cohen, "Oligodeoxynucleotides as Inhibitors of Gene Expression: A Review" *Cancer Res.* 48: 2659–2688 (1988).
Thompson and Gillespie, "Current Concepts in Quantitative Molecular Hybridization" Clin. Biochem 23: 261–266 (1990).

(List continued on next page.)

*Primary Examiner*—Jacqueline M. Stone
*Assistant Examiner*—D. Curtis Hogue, Jr.
*Attorney, Agent, or Firm*—Woodcock Washburn Kurtz Mackiewicz & Norris LLP

[57] ABSTRACT

Oligonucleotides capable of inhibiting the production of proliferation-associated proteins are provided. Oligonucleotides designed to be hybridizable with nucleic acids encoding nucleolar proteins are believed to be therapeutically useful. Certain of such oligonucleotides, hybridizable to portions of the gene coding for p120, especially the 3' untranslated region, were made and found to inhibit the synthesis of p120. The oligonucleotides of the invention are useful for the treatment of diseases characterized by hyperproliferation of cells such as malignancies, inflammatory and cardiovascular diseases. Treatment of human breast cell carcinoma, human epitheloid cervix carcinoma, human amelanotic melanoma, human renal cell carcinoma and other tumors are indicated.

4 Claims, 13 Drawing Sheets

OTHER PUBLICATIONS

Zon, "Oligonucleotide Analogues as Potential Chemotherapeutic Agents", Pharmaceutical Research 5: 539–549 (1988).

Busch, et al., "Rabbit Antibodies to Nucleoli of Novikoff Hepatoma and Normal Liver of the Rat" *Cancer Res.* 34: 2362–2367 (1974).

Busch et al., "Liver Antigens Detected by Liver Antinucleolar Antibodies (40416)" *Proc. Soc. Exp. Biol. Med.* 160: 185–191 (1979).

Chiang et al., "Antisense Oligonucleotides Inhibit Intercellular Adhesion Molecule 1 Expression by Two Distinct Mechanisms" *J. Biol. Chem.* 18162–18171 (1991).

Davis et al., "Nucleolar Antigen Found in Several Human Tumors but not in the Nontumor Tissues Studied" *Proc. Natl. Acad. Sci. U. S. A.* 76: 892–896 (1979).

Hazlewood et al., "mRNA Levels for Human Nucleolar Protein P120 in Tumor and Nontumor Cells", Cancer Communications 01: 29–34 (1989).

Busch et al., "A Nucleolar Antigen Found in a Broad Range of Human Malignant Tumor Specimens" *Cancer Res.* 39: 3024–3030 (1979).

Saijo et al., "Pharmacology of P120 Antisense Oligonucleotide Phosphorothioates in Vitro" Experimental Biology 93 Abstract.

Smetana et al., "Nuclear Aberrations in Human Tumor Cells Following Treatment with P120 Antisense Oligonucleotide ISIS–3466" 1993 AACR ABstract Form.

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
        ( A ) LENGTH: 15
        ( B ) TYPE: Nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 1:

AAAGCCCCC ACCAC                                            1 5

( 2 ) INFORMATION FOR SEQ ID NO: 2:

( i ) SEQUENCE CHARACTERISTICS:
        ( A ) LENGTH: 20
        ( B ) TYPE: Nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 2:

CCCCATGGTA CTGTGGCAGG                            2 0

( 2 ) INFORMATION FOR SEQ ID NO: 3:

( i ) SEQUENCE CHARACTERISTICS:
        ( A ) LENGTH: 20

(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 3:

GGAGAAGGTG GCGTCGCGCG   20

(2) INFORMATION FOR SEQ ID NO: 4:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 4:

CCTTCCTCCC GCTGAGCCCC   20

(2) INFORMATION FOR SEQ ID NO: 5:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 5:

CGGTCAAAGC CCCCCACCAC   20

(2) INFORMATION FOR SEQ ID NO: 6:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 6:

TCCCAGTCCC ACCTCCCATC   20

(2) INFORMATION FOR SEQ ID NO: 7:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes (xi) SEQUENCE DESCRIPTION: SEQ ID NO: 7:

AAGCGGCAAA GGCAGCACCC   20

(2) INFORMATION FOR SEQ ID NO: 8:

(i) SEQUENCE CHARACTERISTICS:
(A) LENGTH: 20
(B) TYPE: nucleic acid
(C) STRANDEDNESS: single
(D) TOPOLOGY: linear (iv) ANTI-SENSE: yes ( x i ) SEQUENCE DESCRIPTION: SEQ ID NO: 8:

CGGTCAAAGC CCCCCACCAC        20

( 2 ) INFORMATION FOR SEQ ID NO: 9:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 9:

CACCCGCCTT GGCCTCCCAC        20

( 2 ) INFORMATION FOR SEQ ID NO: 10:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO:10:

GGGATTCACA GGCATGAGCC        20

( 2 ) INFORMATION FOR SEQ ID NO: 11:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 11:

CGCCACCACA CCCGGCTGAT        20

( 2 ) INFORMATION FOR SEQ ID NO: 12:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 12:

TCTCGAACAC CTGACCTCAG        20

( 2 ) INFORMATION FOR SEQ ID NO: 13:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 13:

CAAAAATACT CAGTGGCCAG        20

(2) INFORMATION FOR SEQ ID NO: 14:

(i) SEQUENCE CHARACTERISTICS:
　　　　(A) LENGTH: 20
　　　　(B) TYPE: nucleic acid
　　　　(C) STRANDEDNESS: single
　　　　(D) TOPOLOGY: linear (iv) ANTI-SENSE: yes (xi) SEQUENCE DESCRIPTION: SEQ ID NO: 14:

```
CACCCGCCTT GGCCTCCCAG                                    20
```

(2) INFORMATION FOR SEQ ID NO: 15:

(i) SEQUENCE CHARACTERISTICS:
　　　　(A) LENGTH: 20
　　　　(B) TYPE: nucleic acid
　　　　(C) STRANDEDNESS: single
　　　　(D) TOPOLOGY: linear (iv) ANTI-SENSE: yes (xi) SEQUENCE DESCRIPTION: SEQ ID NO: 15:

```
CACGCCTCCC GACTCTGCCC                                    20
```

(2) INFORMATION FOR SEQ ID NO: 16:

(i) SEQUENCE CHARACTERISTICS:
　　　　(A) LENGTH: 20
　　　　(B) TYPE: nucleic acid
　　　　(C) STRANDEDNESS: single
　　　　(D) TOPOLOGY: linear (iv) ANTI-SENSE: no (xi) SEQUENCE DESCRIPTION: SEQ ID NO: 16:

```
GTGGGAGGCC AAGGCGGGTG                                    20
```

OLIGONUCLEOTIDE MODULATION OF CELL GROWTH

CROSS-REFERENCE TO RELATED APPLICATION

This application is a 371 of PCT/US93/00754, filed Jan. 27, 1993, which is in turn a continuation-in-part of U.S. patent application Ser. No. 07/841,660, filed Feb. 19, 1992, now abandoned, the entire contents of which are hereby incorporated by reference.

GOVERNMENT RIGHTS

Portions of this work may have been supported by the Cancer Research Center, grant PHS-10893, awarded by the National Cancer Institute, Department of Human Services, USPHS. The United States Government may have certain rights in this invention.

FIELD OF THE INVENTION

This invention relates to diagnostics, research reagents, and therapies for disease states which respond to modulation of the synthesis or metabolism of cell proliferation-associated proteins. In particular, this invention relates to oligonucleotides which inhibit the production of a group of proteins which are synthesized in proliferating cells. Oligonucleotides designed to hybridize to the mRNA encoding p120 are provided to effect these goals. These oligonucleotides have been found to lead to modulation of the synthesis and metabolism of cell proliferation-associated proteins. Palliation and therapeutic effect result.

BACKGROUND OF THE INVENTION

Malignant neoplasms have several characteristics which distinguish them from benign tumors and normal cells. These features include uncontrolled cell growth, invasiveness and metastasis. Malignant tumors may be differentiated from benign tumors or normal cells by morphological characteristics including anaplastic cells, increased mitotic index, abnormal mitotic cells, variable size and shape, increased nuclear to cytoplasmic ratio, and large prominent nucleoli. Much research has been focused on the biochemical and genetic characterization of malignant cells attempting to identify differences responsible for these phenotypic changes. Such studies have lead to the identification of so-called "oncogenes" which, if overexpressed or mutated, promote malignant transformation of cells.

Current agents which affect cellular proliferation are nonspecific cytotoxic agents such as DNA alkylating agents, DNA intercalators or microtubule depolymerizing agents. These agents all suffer from severe toxicities and lack of specificity towards the malignant cell. Thus, there is a long-felt need for molecules which effectively inhibit proliferation of malignant cells. Oligonucleotides designed to hybridize with nucleic acids encoding proliferation— associated proteins represent a novel approach to selectively inhibit gene expression, in particular expression of p120.

OBJECTS OF THE INVENTION

It is a principle object of the invention to provide therapies for diseases with a component due to hyperproliferation of cells, such as malignancies, inflammatory diseases and cardiovascular diseases, through perturbation in the synthesis and expression of proliferating cell nucleolar antigens.

It is a further object of the invention to provide oligonucleotides and other compositions which are capable of inhibiting the function of nucleic acids encoding proliferation associated proteins.

A further object is to provide oligonucleotides which, regardless of mechanism, inhibit the growth or development of malignant cells, especially human breast carcinoma cells.

These and other objects of this invention will become apparent from a review of the instant specification.

SUMMARY OF THE INVENTION

Figure 1A:
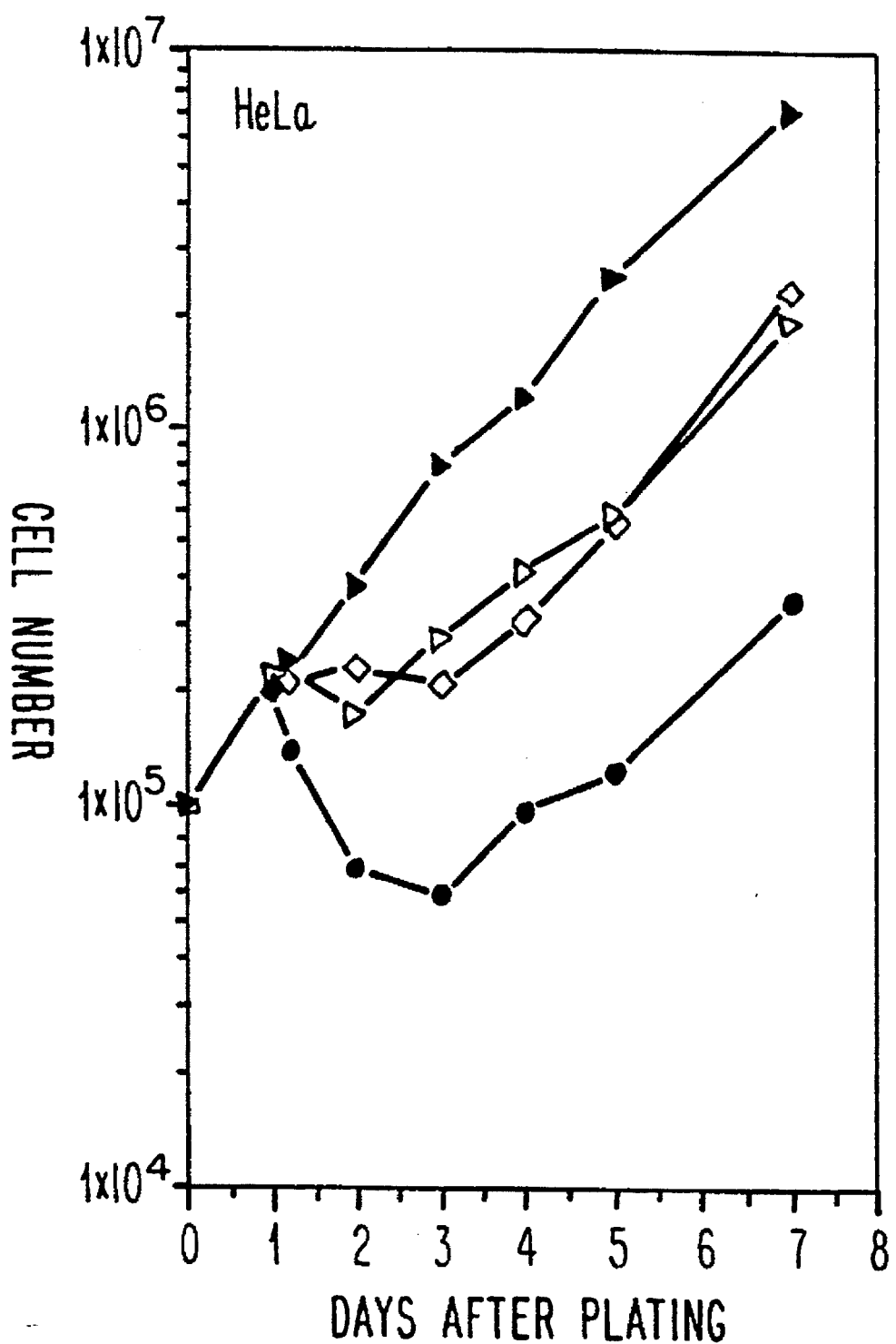
FIG. 1 depicts screening of treatment conditions of cells with oligonucleotides in accordance with the invention. Panel A shows a representative growth curve of HeLa cells in serum-free medium treated with antisense oligonucleotides SEQ ID NO: 3 (open diamonds), SEQ ID NO: 5 (open triangles), SEQ ID NO: 9 (filled circles) plus DOTMA for four hours. Panel B shows a representative growth curve of HeLa cells in serum-containing complete medium treated with antisense oligonucleotides SEQ ID NO: 3, SEQ ID NO: 5, SEQ ID NO: 9 without DOTMA for twenty-four hours. Panel C shows a representative growth curve of HeLa cells treated with antisense oligonucleotide SEQ ID NO: 9 with DOTMA for four hours in serum containing medium (filled squares) or in serum free medium (filled circles), or DOTMA without antisense oligonucleotide in serum free medium (triangles).

In accordance with the present invention, oligonucleotides are provided which are designed to specifically hybridize with all or a portion of nucleic acids encoding proliferation associated proteins. The oligonucleotides are able to inhibit the production of the proliferation associated proteins.

The mechanism of action of these oligonucleotides is unknown. They may function to interfere with the function of mRNA; either its translation into protein, its translocation into the cytoplasm, its transcription from DNA or any other activity necessary to its overall biological function may be affected. The failure of the RNA to perform all or part of its function would result in failure of a portion of the genome controlling protein synthesis to be properly expressed. It has been discovered that the genes coding for protein p120 are particularly useful for this approach. Inhibition of p120 expression may be useful for the treatment of cancers and inflammatory diseases. It is also possible that the mechanism of action of the oligonucleotides of this invention is not related to interference with mRNA function, either being expressed themselves or otherwise having an undefined mechanism of action which, nonetheless, is toxic to the target cells.

Methods of modulating cell proliferation with an effective amount of an oligonucleotide hybridizable with nucleic acids encoding a proliferation associated protein are provided. Oligonucleotides hybridizable with nucleic acids coding for p120 are preferred. It is also preferred that such oligonucleotides have from about 12 to 50 nucleic acid subunits. Contacting cells to modulate proliferation with such oligonucleotides regardless of mechanism is also contemplated hereby.

DETAILED DESCRIPTION OF THE INVENTION

It has been found that certain nucleolar proteins are implicated in hyperproliferative disease, especially certain cancers. The pleomorphism and hyperactivity of nucleoli characteristic of malignant cells prompted studies attempting to identify differences between normal and malignant nucleoli. Early experiments attempting to identify nucleolar proteins which were expressed only in malignant cells, utilized rabbits immunized with nucleoli isolated from malignant cells and preabsorption of the sera with nucleolar extracts isolated from normal cells Busch, et al., Cancer Res. 34:2362-2367 (1974); Busch et al., Proc. Soc. Exp. Biol. Med., 160:185-191 (1979); Davis et al., Proc. Natl. Acad. Sci. U.S.A., 76:892-896 (1979); Busch et al., Cancer Res., 39:3024-3030 (1979). These studies resulted in the identification of rabbit antisera which reacted with a broad range of human cancers but not normal human tissues. The major problem of this type of an approach was the difficulties associated with rabbit antibodies in terms of reproducibility between animals, variable titer and polyclonal nature of the antibodies.

Based upon the initial positive results with polyclonal rabbit antiserum, efforts were made to purify and characterize tumor specific nucleolar proteins. Proteins with molecular weights ranging from 54,000 to 68,000 were purified from either rat or human tumors which were not found in the normal tissues examined. Chan et al., Transplant. Proc., 8:1955-1957 (1981); Chan et al., Cancer Res., 40:3194-3201 (1980); Chan et al., J. Cancer Res. Clin. Oncol., 103:7-16 (1982); Takahashi et al., Cancer Res. Clin. Oncol., 105:67-75 (1983). Two-dimensional gel analysis of nucleolar proteins isolated from malignant and normal tissues also identified several proteins unique to malignant cells. Spohn et al. Cancer Invest. 3:307-320 (1985).

Because of the lack of reproducibility of polyclonal antiserum, monoclonal antibodies to human tumor nucleolar antigens were developed. These studies resulted in the identification of several proteins associated with proliferating cells but undetected from normal quiescent cells. These monoclonal antibodies were demonstrated to react with a 145 kDa protein, a 40 kDa protein and a 120 kDa protein Freeman et al., Cancer Res., 46:3593-3598 (1986); Chatterjee et al., Cancer Res., 47:1123-1129 (1987); Freeman et al., Cancer Res., 48:1244-1251 (1988). These antigens were found to be expressed in a similar manner as the cyclins during the G1 to S phase of the cell cycle as shown by Matthews et al., Nature, 3009:374-376 (1983).

The 120 kDa nucleolar antigen (p120) was of particular interest in that it was detected in a wide variety of human malignancies but not in most normal tissues. Further studies suggested that p120 may be a prognostic marker in breast cancer in that patients with p120 negative tumors had a good prognosis while patients with p120 positive tumors had a poor prognosis Freeman et al., Cancer Res., 51:1973-1978 (1991). The p120 antigen is apparently related to the proliferative state of the cell and nucleolar hyper-reactivity. In support of this conclusion was the finding that microinjection of p120 antibodies into tumor cells decreases their proliferative rate and induces a compaction of the nucleolus. Freeman and Bondada, Am. Assoc. Cancer Res., 31:261 (1990). p120 has, however, also been identified in small amounts in normal proliferating tissues as shown by Freeman et al., Cancer Res., 48:1244-1251 (1988).

Multiple overlapping cDNA clones for p120 were isolated and sequenced; the genomic DNA sequence was also determined. Busch et al., Cancer Res., 50:4830-4838 (1990); Fonagy et al., Cancer Commun., 1:243-245 (1989); Larson et al., Cancer Commun., 2:63-71 (1990). Four major domains were identified in the p120 protein, a basic amino terminal domain, followed by an acidic domain, a hydrophobic domain, and a domain rich in proline and cysteine residues. A search of the computer data bases did not reveal any significant homology between p120 and other known proteins other than an acidic domain shared by other nucleolar proteins. The gene for p120 was subsequently demonstrated to be 12 kB in length, composed of 15 exons and 14 introns Larson et al., Cancer Comm., 2:63-71 (1990).

The function of p120 in proliferating cells is currently unknown. The protein was identified as a component of the nucleolar matrix, associated with a network of 20 to 30 nm beaded fibrils Ochs et al., Cancer Res., 48:6523-6529 (1988). Roles suggested for p120 include transcription of ribosomal RNA or replication of ribosomal DNA or a structural role in the nucleolar matrix. As exemplified by microinjection of monoclonal antibodies to p120 Freeman and Bondada, *Am. Assoc. Cancer Res.*, 31:261 (1990), inhibiting p120 expression would decrease proliferation of malignant cells.

Constructs designed to be antisense to all or a portion of a gene coding for a nucleolar protein, p120, have been found to inhibit the growth of human breast carcinoma cells in culture. Saijo, et al., *Cancer Letters*, in press. It is believed that other hyperproliferative diseases may be similarly treated with oligonucleotides designed to be complementary to genes coding for nucleolar proteins.

Antisense oligonucleotides hold great promise as therapeutic agents for the treatment of many human diseases. Conceptually, it is much easier to design compounds which interact with a primary structure such as an RNA molecule by base pairing than it is to design a molecule to interact with the active site of an enzyme or ligand binding site of a receptor. Oligonucleotides specifically bind to the complementary sequence of either pre-mRNA or mature mRNA, as defined by Watson-Crick base pairing, inhibiting the flow of genetic information from DNA to protein. The properties of antisense oligonucleotides which make them specific for their target sequence also makes them extraordinarily versatile. Because antisense oligonucleotides are long chains of four monomeric units they may be readily synthesized for any target RNA sequence. Numerous recent studies have documented the utility of antisense oligonucleotides as biochemical tools for studying target proteins. Rothenberg et al., *J. Natl. Cancer Inst.*, 81:1539–1544 (1989); Zon, G., *Pharmaceutical Res.* 5:539–549 (1988). Because of recent advances in oligonucleotide chemistry, synthesis of nuclease resistant oligonucleotides, and oligonucleotide analogs which exhibit enhanced cellular uptake, it is now possible to consider the use of antisense oligonucleotides as a form of therapeutics.

Oligonucleotides offer an ideal solution to the problems encountered in prior art approaches. They can be designed to selectively inhibit the production of an enzyme, and they avoid non-specific mechanisms such as free radical scavenging or binding to multiple receptors. A complete understanding of enzyme mechanism or receptor-ligand interactions is not needed to design specific inhibitors.

For therapeutics, methods of modulating cell proliferation are provided. Oligonucleotides designed in accordance with this invention contact selected cells. Persons of ordinary skill can easily determine optimum dosages, dosing methodologies and repetition rates. Such treatment is generally continued until either a cure is effected or a diminution in the disease state is achieved. Long term treatment is likely for some diseases.

The formulation of therapeutic compositions and their subsequent administration is believed to be within the skill in the art. In general, for therapeutics, a patient suspected of needing such therapy is given an oligonucleotide in accordance with the invention, commonly in a pharmaceutically acceptable carrier, in amounts and for periods which will vary depending upon the nature of the particular disease, its severity and the patients overall condition. The pharmaceutical compositions of this invention may be administered in a number of ways depending upon whether local or systemic treatment is desired, and upon the area to be treated. Administration may be topically (including ophthalmically, vaginally, rectally, intranasally), orally, or parenterally, for example by intravenous drip, subcutaneous, intraperitoneal or intramusular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms and the like may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The present invention is also suitable for diagnosing hyperproliferative states in tissue or other samples from patients suspected of having a hyperproliferative disease. Thus, the ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition.

The oligonucleotides of this invention may also be used for research purposes. Thus, the specific hybridization exhibited by the oligonucleotides may be used for assays, purifications, cellular product productions and in other methodologies which may be appreciated by persons of ordinary skill in the art.

The present invention employs oligonucleotides designed to be specifically hybridizable with nucleic acids encoding proliferation associated proteins. Such oligonucleotides are termed "antisense" since they are complementary to the "sense" nucleic acids which so encode. In accordance with this invention, it is not required that such oligonucleotides actually perform in accordance with an antisense methodology, binding with and inhibiting mRNA, but only that they be designed to be complementary to at least a portion of a gene coding a nucleolar protein.

It has now been found that certain oligonucleotides designed to be antisense to portions of the nucleolar protein p120 DNA are particularly useful for interfering with cell hyperproliferation. While a number of such oligonucleotides have been found to have some activity, oligonucleotides directed to the 3' untranslated region have been found to have particular activity. Of these, the oligonucleotide sequences:

| 5' | | 3' | |
|---|---|---|---|
| CACCCGCCTT | GGCCTCCCAC | (SEQ ID NO: 9), or | |
| CACCCGCCTT | GGCCTCCCAG | (SEQ ID NO: 14) | | have demonstrated high activity in inhibiting the growth of a number of human cancers.

In accordance with the invention, oligonucleotides believed to be useful are those which are designed to be specifically hybridizable with nucleic acid coding for all or a portion of a nucleolar protein, especially one associated with hyperproliferative disease. The protein p120 is a particular target. It has also been found that for p120, targeting the 3' untranslated region of the DNA coding for the protein is particularly useful, giving rise to the oligonucleotides set forth above.

It is not necessary that oligonucleotides be identical to the ones set forth with specificity herein. It is sufficient if effective portions of the oligonucleotides are employed. Preferred oligonucleotides, those having from 12 to about 50 nucleotide subunits, need not include all twenty of the subunits of the preferred oligonucleotides. It is sufficient if an effective portion of the oligonucleotides are incorporated therein. Accordingly, oligonucleotides which have, for example, twenty-five subunits, fifteen of which are within the sequences set forth herein, may have good utility in the practice of certain embodiments of this invention. Additionally, substitution of one or more subunits within a sequence may be undertaken without deviating from the spirit of the invention so long as an effective portion of the oligonucleotide is retained.

In the context of this invention, the term "oligonucleotide" refers to a polynucleotide formed from naturally occurring bases and furanosyl groups joined by native phosphodiester bonds. This term effectively refers to naturally occurring species or synthetic species formed from naturally occurring subunits or their close homologs. The term "oligonucleotide" may also refer to moieties which function similarly to naturally occurring oligonucleotides but which have non-naturally occurring portions. Thus, oligonucleotides may have altered sugar moieties or intersugar linkages. Exemplary among these are the phosphorothioate and other sulfur-containing species which are known for use in the art.

In accordance with certain preferred embodiments, at least some of the phosphodiester bonds of the oligonucleotide are substituted with a structure which functions to enhance the ability of the compositions to penetrate into the region of cells where the RNA whose activity to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the furanosyl portion of the nucleotide subunits may also be effected, as long as the essential tenets of this invention are adhered to. Examples of such modifications are 2'-O-alkyl- and 2'-halogen-subsituted nucleotides. Some specific examples of modifications at the 2' position of sugar moieties which are useful in the present invention are OH, SH, SCH$_3$, F, OCH$_3$, OCN, O(CH$_2$)$_n$NH$_2$ or O(CH$_2$)$_n$CH$_3$ where n is from 1 to about 10, and other substituents having similar properties.

Such oligonucleotides are best described as being functionally interchangeable with natural oligonucleotides (or synthesized oligonucleotides along natural lines), but which have one or more differences from natural structure. All such oligonucleotides are comprehended by this invention so long as they function effectively to hybridize with the selected RNA. The oligonucleotides in accordance with this invention preferably comprise from about 12 to about 50 nucleic acid base units. It is more preferred that such oligonucleotides comprise from about 12 to 25 nucleic acid base units. As will be appreciated, a nucleic acid base unit is a base-sugar combination suitably bound to adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, a 5' cap region, an intron/exon junction, coding sequences or sequences in the 5'- or 3'-untranslated region.

In accordance with this invention, the oligonucleotide is specifically hybridizable with nucleic acids encoding a protein involved in the proliferation of cells. In preferred embodiments, the protein is p120. Oligonucleotides comprising the corresponding, specifically hybridizable, sequence, or part thereof, are useful in the invention.

Several preferred embodiments of this invention are exemplified in accordance with the following examples. The target mRNA species for modulation relates to p120. Persons of ordinary skill in the art will appreciate that the present invention is not so limited, however, and that it is generally applicable. The inhibition or modulation of production of the p120 are expected to have significant therapeutic benefits in the treatment of disease.

The invention is further illustrated in the following, non-limiting examples.

EXAMPLE 1

Synthesis and Characterization of Oligonucleotides and Analogs

Unmodified DNA oligonucleotides were synthesized on an automated DNA synthesizer (Applied Biosystems model 380B) using standard phosphoramidite chemistry with oxidation by iodine. β-cyanoethyldiisopropyl phosphoramidites were purchased from Applied Biosystems (Foster City, Calif.). For phosphorothioate oligonucleotides, the standard oxidation bottle was replaced by a 0.2M solution of H-1,2-benzodithiole-3-one 1,1-dioxide in acetonitrile for the stepwise thiation of the phosphite linkages. The thiation cycle wait step was increased to 68 seconds and was followed by the capping step. 2'-O-methyl phosphorothioate oligonucleotides were synthesized using 2'-O-methyl β-cyanoethyldiisopropylphosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Trisborate buffer, pH 7.0. Oligodeoxynucleotides and their phosphorothioate analogs were judged from electrophoresis to be greater than 80% full length material.

The relative amounts of phosphorothioate and phosphodiester linkages obtained by this synthesis were periodically checked by $^{31}P$ NMR spectroscopy. The spectra were obtained at ambient temperature using deuterium oxide or dimethyl sulfoxide-$d_6$ as solvent. Phosphorothioate samples typically contained less than one percent of phosphodiester linkages.

For determination of oligonucleotide concentration, $OD_{260}$ absorbance was calculated from the OD units using the equation: OD=E×C, where OD is the absorbance at 260 nm, E is the, mM extinction coefficient for the entire oligonucleotide, and C is the concentration in mM; Sambrook, et al., 1989 *Molecular Cloning. A Laboratory Manual*, Cold Spring Harbor Laboratory Press: Cold Spring Harbor, 2nd ed. The oligonucleotide solutions were sterilized by filtration through 0.2 μm cellulose acetate centrifugal microfilter units (Centrex, Schleicher & Schuell) by centrifugation at 1500 g for 10 minutes at 4° C. The concentrations of oligodeoxynucleotides were determined after filtration as described above: the concentrations were adjusted to 100 μM and the solutions were kept at 4° C. Oligonucleotides having the sequences shown in Table 1 were made.

TABLE I

| SEQUENCE | SEQ ID NO: (IDENT. NO.) | REGION |
| --- | --- | --- |
| AAAGCCCCCC ACCAC | 1 | Coding |
| CCCCATGGTA CTGTGGCAGG | 2 | AUG Codon |
| GGAGAAGGTG GCGTCGCGCG | 3 | 5' UTR |
| CCTTCCTCCC GCTGAGCCCC | 4 | Coding |
| CGGTCAAAGC CCCCCACCAC | 5 | Coding |
| TCCCAGTCCC ACCTCCCATC | 6 | 3' UTR |
| AAGCGGCAAA GGCAGCACCC | 7 | 3' UTR |
| CGGTCAAAGC CCCCCACCAC | 8 | Coding |
| CACCCGCCTT GGCCTCCCAC | 9 | 3' UTR |
| GGGATTCACA GGCATGAGCC | 10 | 3' UTR |
| CGCCACCACA CCCGGCTGAT | 11 | 3' UTR |
| TCTCGAACAC CTGACCTCAG | 12 | 3' UTR |
| CAAAAATACT CAGTGGCCAG | 13 | Stop Codon |
| CACCCGCCTT GGCCTCCCAG | 14 | 3' UTR |
| CACGCCTCCC GACTCTGCCC | 15 | Randomized |
| GTGGGAGGCC AAGGCGGGTG | 16 | sense |

EXAMPLE 2

Cell Lines

HeLa S3 (ATCC CCL 2.2, human epithelioid cervix carcinoma) cells were subcultured in Dulbecco's modified Eagle Medium (D-MEM) (GIBCO BRL), supplemented with 10% fetal bovine serum (FBS) (GIBCO BRL) and 1% penicillin-streptomycin liquid (100 000 IU/ml penicillin G sodium, 10 mg/ml streptomycin sulfate in 0.85% saline) (GIBCO BRL). LOX (IMVI, human amelanotic melanoma) cells (provided by Dr. D. J. Dykes, Southern Research Institute, Birmingham, Ala.) were subcultured in RPMI 1640 medium (RPMI) (GIBCO BRL) supplemented with 10% FBS and 1% penicillin-streptomycin liquid. HRCC-SN12A1 (human renal cell carcinoma) cells (established from the ascitic cells of intrarenally transplanted HRCC-bearing nude mouse and provided by Dr. I. J. Fidler, M.D., Anderson Cancer Center, Houston, Tex.)(Naito, etal., 1986) were subcultured in Eagle minimum essential medium (MEM) (GIBCO BRL), supplemented with 10% FBS, vitamins, L-glutamine, sodium pyruvate, non-essential amino acids and 1% penicillin-streptomycin liquid. All cells were negative for mycoplasma infection as determined by a DNA stain (McGarrity, *Methods in Enzymology: Cell Culture*, Vol 63, p23 (Academic Press, San Diego; 1979); Freshney, *Culture of Animal Cells: A Manual of Basic Techniques* (Wiley-Liss, NY; 1987).

EXAMPLE 3

Treatment of Cells

Twenty-four hours after plating ($1\times10^5$ cells into 6-well cell culture dishes), the cells growing in monolayer were gently washed once with 5 ml serum-free D-MEM, RPMI and MEM medium for HeLa S3, LOX and HRCC-SN12A1 cells, respectively. Freshly prepared serum-free mediumcontaining 10 μg/ml cationic lipid (DOTMA); Chiang, et al., *J. Biol. Chem.*, 266:18162 (1991); Bennett, et al., *J. Liposome Research*, in press (1992); were mixed with oligonucleotide and preincubated at 37° C. in a humidified incubator for 15 minutes to allow formation of an oligonucleotide-cationic lipid complex. The oligonucleotide concentrations were between 0.001 and 10 μM, but for the majority of the experiments for HeLa S3 cells 0.1 μM, for LOX cells 0.03–0.05–0.1 μM, and for HRCC cells 0.1 μM concentrations were used. After 4 hour incubation (treatment time) at 37° C. in a humidified $CO_2$ incubator, the medium was changed to complete medium containing 10% FBS and 1% penicillin-streptomycin liquid. The cells were cultured at 37° C. in a humidified $CO_2$ incubator for 7 days.

EXAMPLE 4

Determination of Cell Growth

The effect of oligonucleotides on cell growth was determined by counting the attached cells in the 6-well plates through a phase contrast inverted microscope (Nikon Diaphot, 10×objective, 10×ocular, 4×magnification extender, total magnification: 400×). The attached cells on 10 randomly chosen fields were counted (10–200 cells/field) and the total cell number was calculated by multiplying the mean cell number by the correction factor ($f_{6-well}$=6028, $f_{24-well}$=1258, $f_{10\ cm\ dish}$=35,670). The cell number determination was calibrated and standardized in several experiments. The dead floating cells (viability was determined by colony formation) were not counted. The cell number in each well was determined before treatment, immediately after treatment, and daily after treatment for 5–7 days.

EXAMPLE 5

Screening of Oligonucleotides for Ability to Inhibit the Production of p120

In order to assess the effectiveness of the oligonucleotides, assays were performed. In parallel experiments, exponentially growing HeLa cells in monolayer were treated with antisense oligonucleotides designed to hybridize to various regions of the p120 sequence; Fonagy, et al., *Cancer Communications*, 1:243 (1989); Larson, et al., *Cancer Communications*, 2:63 (1990) (Table 1). The oligonucleotides were complexed with cationic lipid (0.1 μM oligonucleotide+10 μg/ml DOTMA in serum-free medium for 4 hours (FIG. 1A) or used alone in serum-free medium (FIG. 1B). Cell growth was monitored as described in Example 4. For plots (Sigmaplot), and for data analysis (Epistat), software packages were used.

Figure 1B:
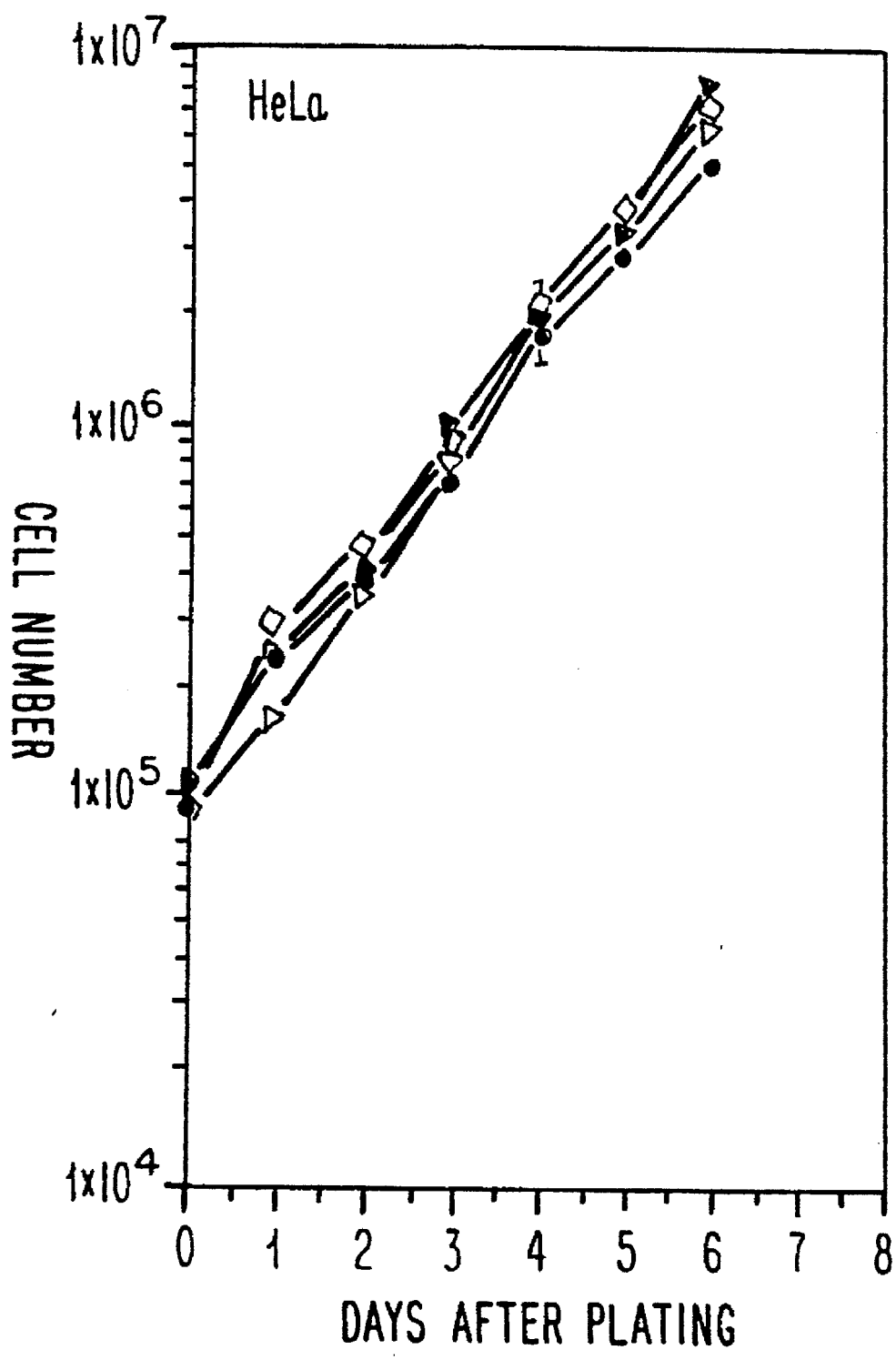

FIG. 1A shows representative growth curves of HeLa cells in the presence of DOTMA and/or oligonucleotides. Inhibition of cell growth was found with several p120 antisense oligonucleotides. The most consistent and greatest inhibition of cell growth was observed with the oligonucleotide having SEQ ID NO: 9 (FIG. 1A, filled circles), which was then used in subsequent experiments. Immediately after treatment, there was no cell detachment or direct cell killing, but 24–48 hours later a cytocidal effect was observed. The rates of cell growth inhibition and the percentage of surviving cells differed with individual oligonucleotides (FIG. 1A).

Figure 1C:
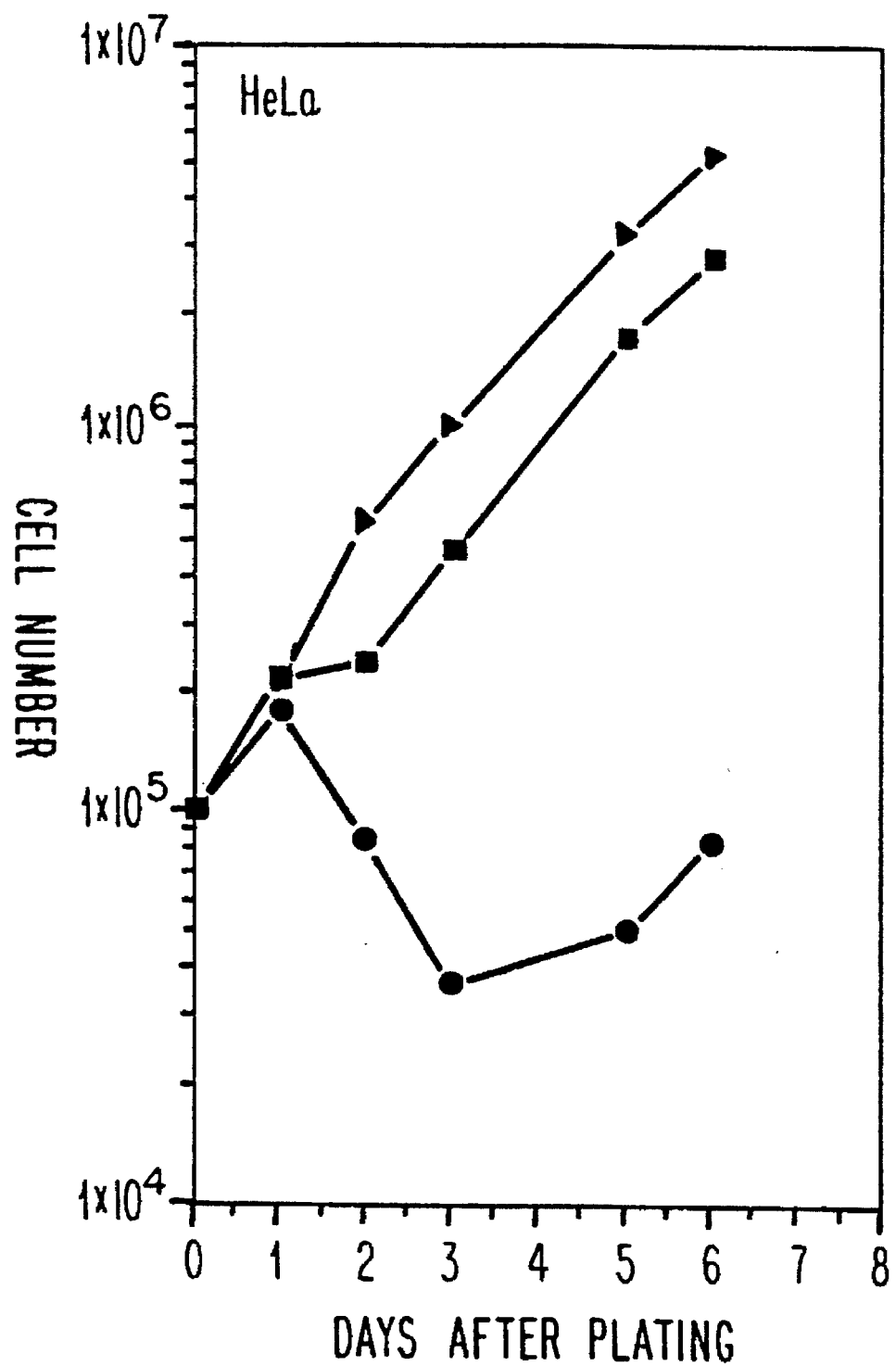

No cytostatic or cytocidal effects were observed with the oligonucleotide alone at concentrations of 0.1–1 μM; in the absence of cationic lipid (24 h in serum-containing medium) (FIG. 1B), the growth rates of the oligonucleotide-treated cells and cells treated with DOTMA alone were the same. Inhibition of cell growth after DOTMA-mediated oligonucleotide treatment in complete (10% FBS) medium was very slight compared to the serum-free condition (FIG. 1C). In the serum-free medium DOTMA was essential for the growth inhibition by oligonucleotide having SEQ ID NO: 9.

In some preliminary experiments, the 4 hour DOTMA-mediated oligonucleotide treatment in serum-free medium was found to be optimal. Extending the time in complete 10% FBS-containing medium for 20 or 60 hours; Bennett, et al., *Molecular Pharmacology*, in press, and Bennett, et al., *J. Liposome Research*, in press (1992); had no additional effect. Accordingly, the cells were incubated with the oligonucleotide-DOTMA complex for 4 hours in serum-free medium.

Two of the oligonucleotides, SEQ ID NO: 9 and SEQ ID NO: 14 were found to have inhibitory activity. These oligonucleotides, which were designed to be complementary to the 3' untranslated region of p120, were tested further as described in Example 6. Others of the oligonucleotides were also found to have some activity (data not shown).

EXAMPLE 6

Oligonucleotide Screening of Preferred Embodiments

Figure 2A:
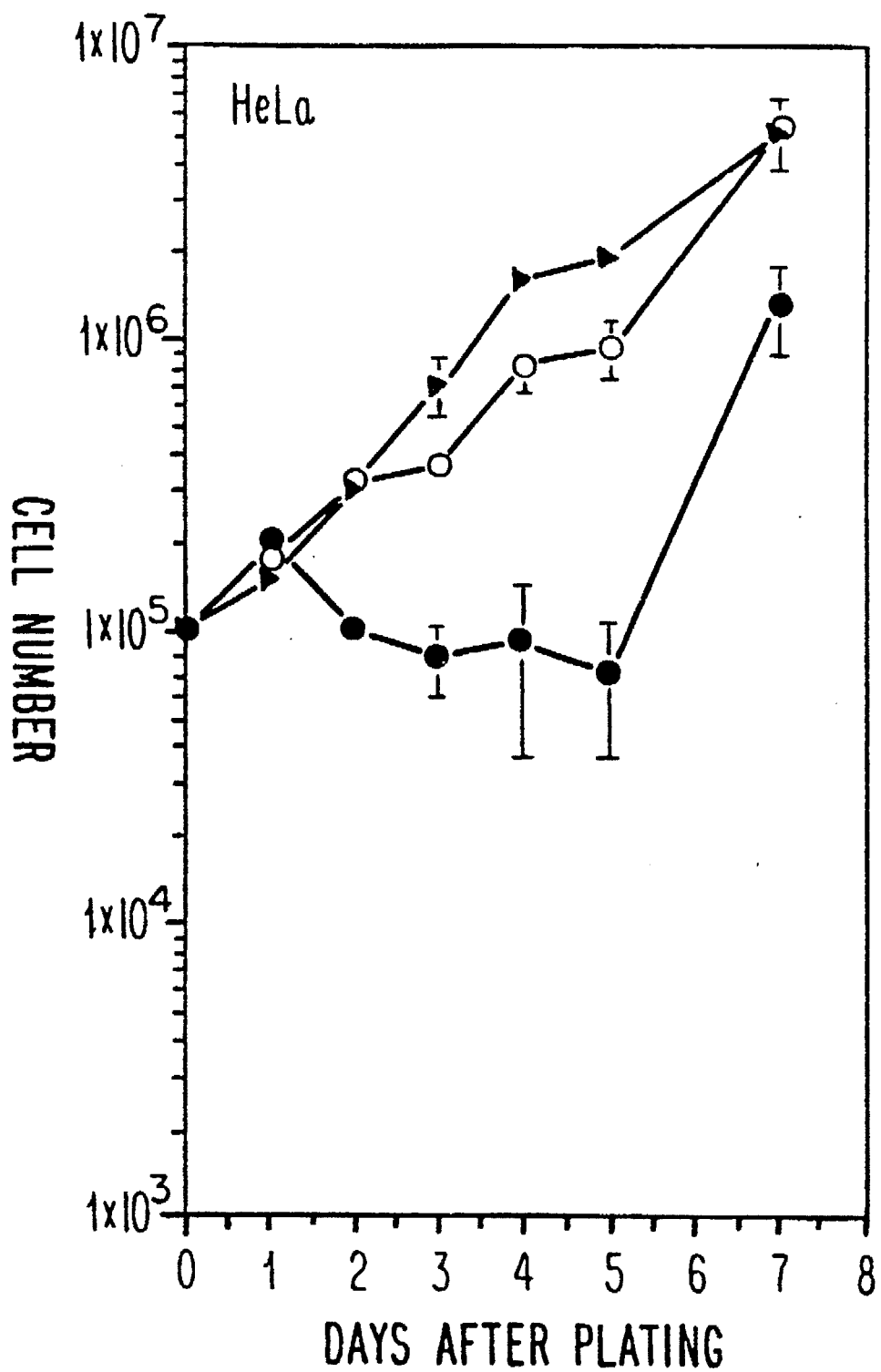
FIG. 2 depicts screenings of certain preferred oligonucleotides in accordance with the invention showing inhibition of tumors. Panel A shows data for 0.1 µM SEQ ID NO: 14+DOTMA (open circles), 0.1 µM SEQ ID NO: 9+DOTMA (filled circles) and a control containing DOTMA without oligonucleotide (filled triangles) against HeLa (human epitheloid cervix carcinoma), Panel B shows data for 0.1 µM SEQ ID NO: 14+DOTMA (open circles), 0.1 µM SEQ ID NO: 9+DOTMA (closed circles) and a control (closed triangles) against LOX (human amelanotic melanoma) while Panel C depicts 0.1 µM and 1.0 µM SEQ ID NO: 14+DOTMA (open circles), 0.1 µM and 1.0 µM SEQ ID NO: 9+DOTMA (closed circles) and a control (closed triangles) against SN12A1 (human renal cell carcinoma) cell lines.
Figure 2B:
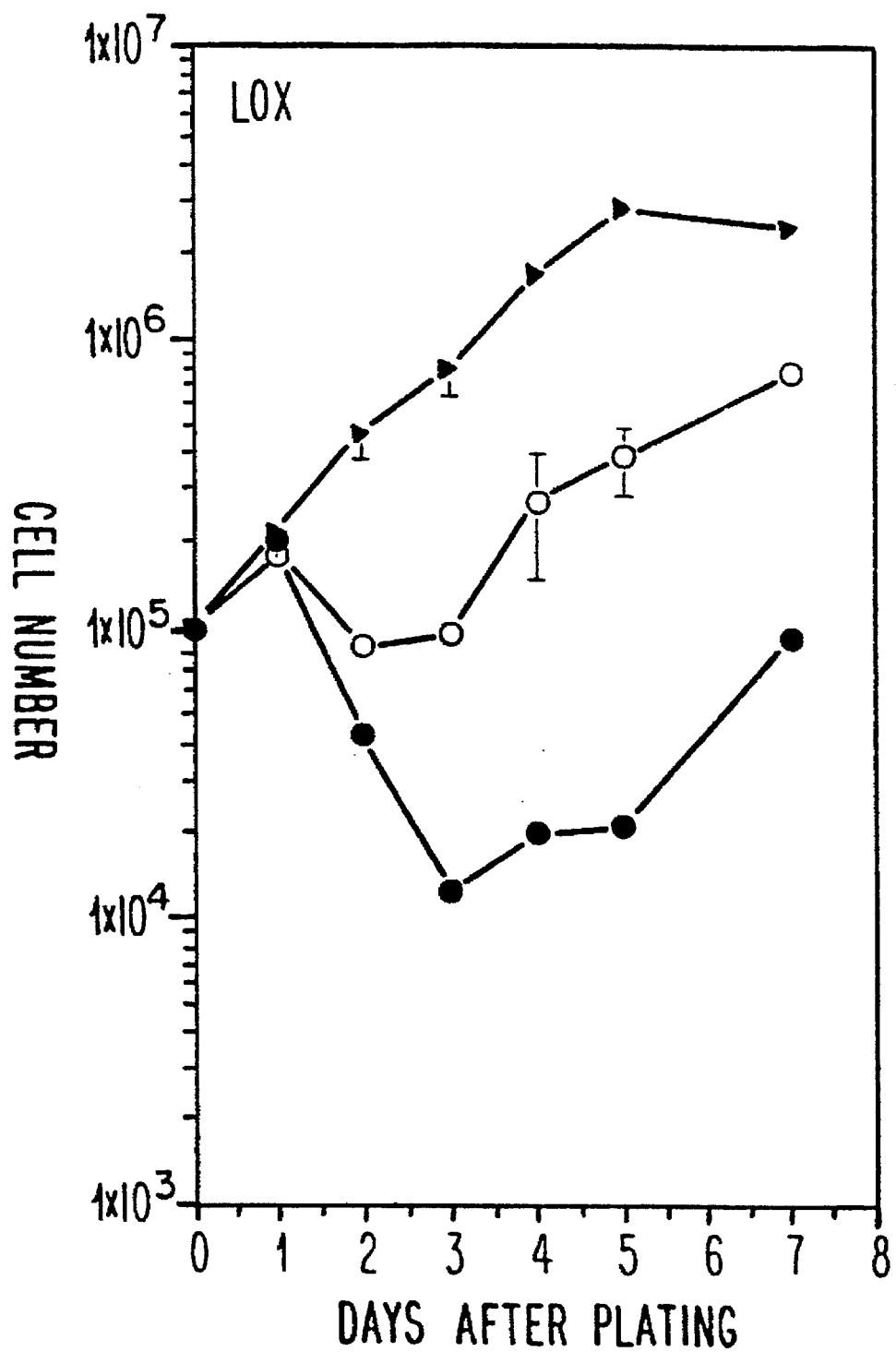
Figure 2C:
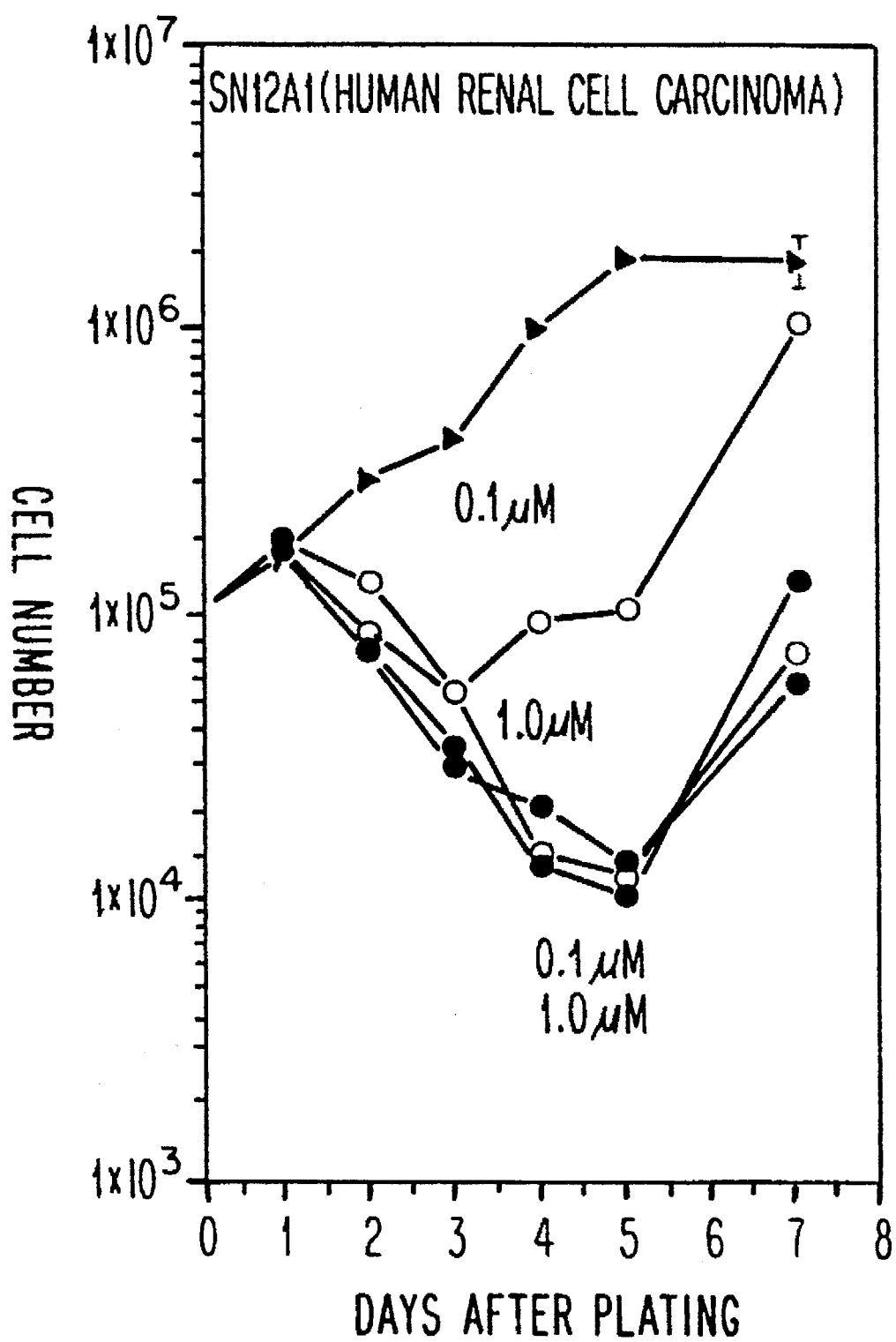

Screening of antisense oligonucleotides for human tumor cell growth inhibition was conducted for SEQ ID NO: 9 and SEQ ID NO: 14. The data are shown in FIG. 2, panels A, B, and C. Panel A shows the results for HeLa (human epitheloid cervix carcinoma) cells while Panel B depicts LOX (human amelanotic melanoma metastasis) cells. Panel C relates data for SN12A1 (human renal cell carcinoma) cells. All testing protocols are conventional and generally similar to the protocol set forth in Example 4. Exponentially growing human tumor cells in monolayers, were treated with 0.1 and 1 μM oligonucleotide+10 μg/ml DOTMA ("Lipofectin" reagent) for 4 hours. Marked cell growth inhibition and 0.5 to 1.5 log-cell kill was observed, especially 3–4 days after treatment with SEQ ID NO: 9. Each of the preferred oligonucleotides showed marked inhibition of the tumors in the respective panels. Use of DOTMA appears to be useful in adjunct with the oligonucleotides.

Figure 3A:
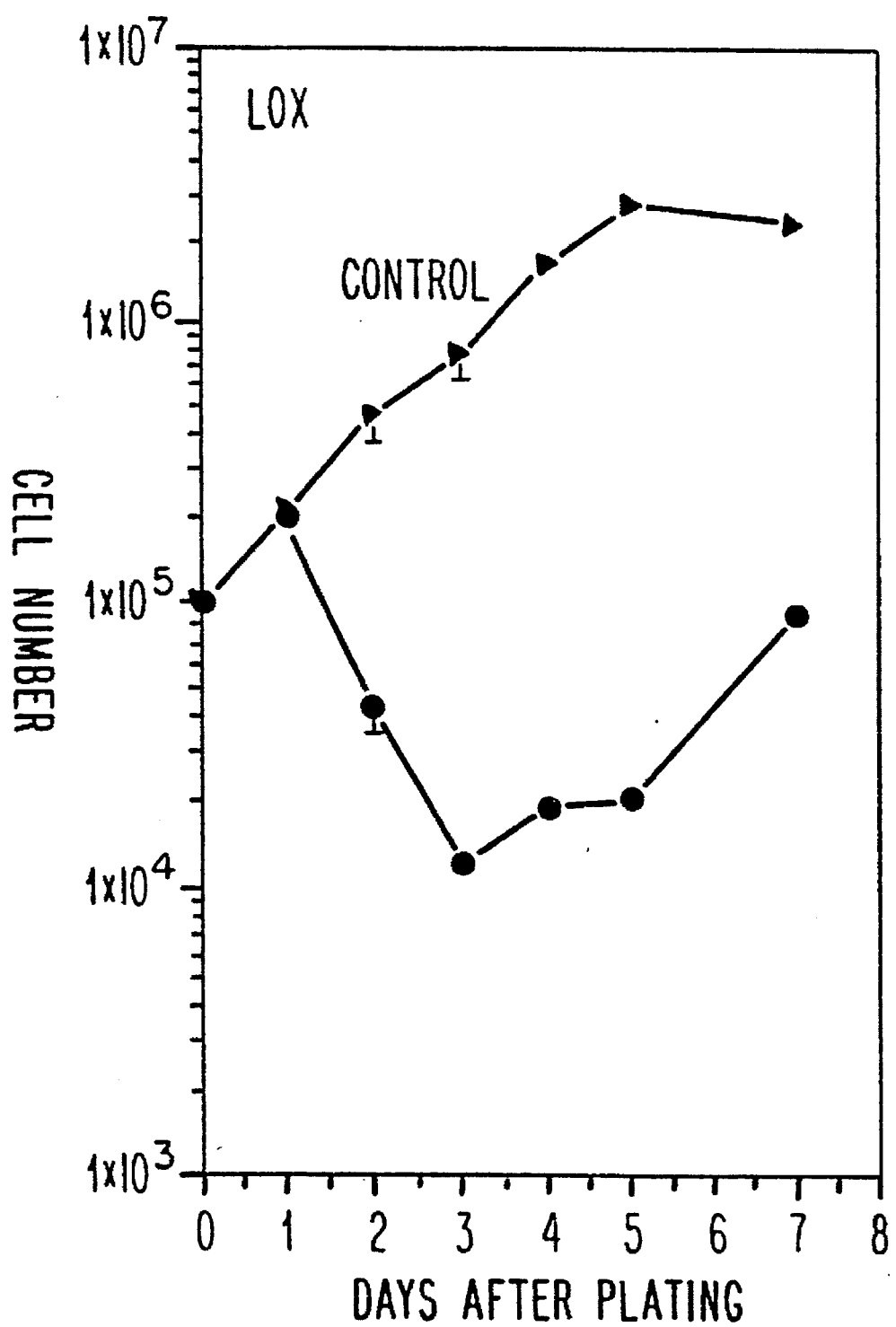
FIG. 3 depicts the inhibitory effect on cell growth of antisense oligonucleotide SEQ ID NO: 9 (filled circle) in different human tumor cell lines as compared to a control (filled triangle) containing DOTMA without oligonucleotide. Panel A shows LOX cells treated with oligonucleotide in the presence of DOTMA for 4 hours in serum-free medium. Panel B shows HRCC (SN12A1) cells treated with oligonucleotide in the presence of DOTMA for 4 hours in serum free medium.
Figure 3B:
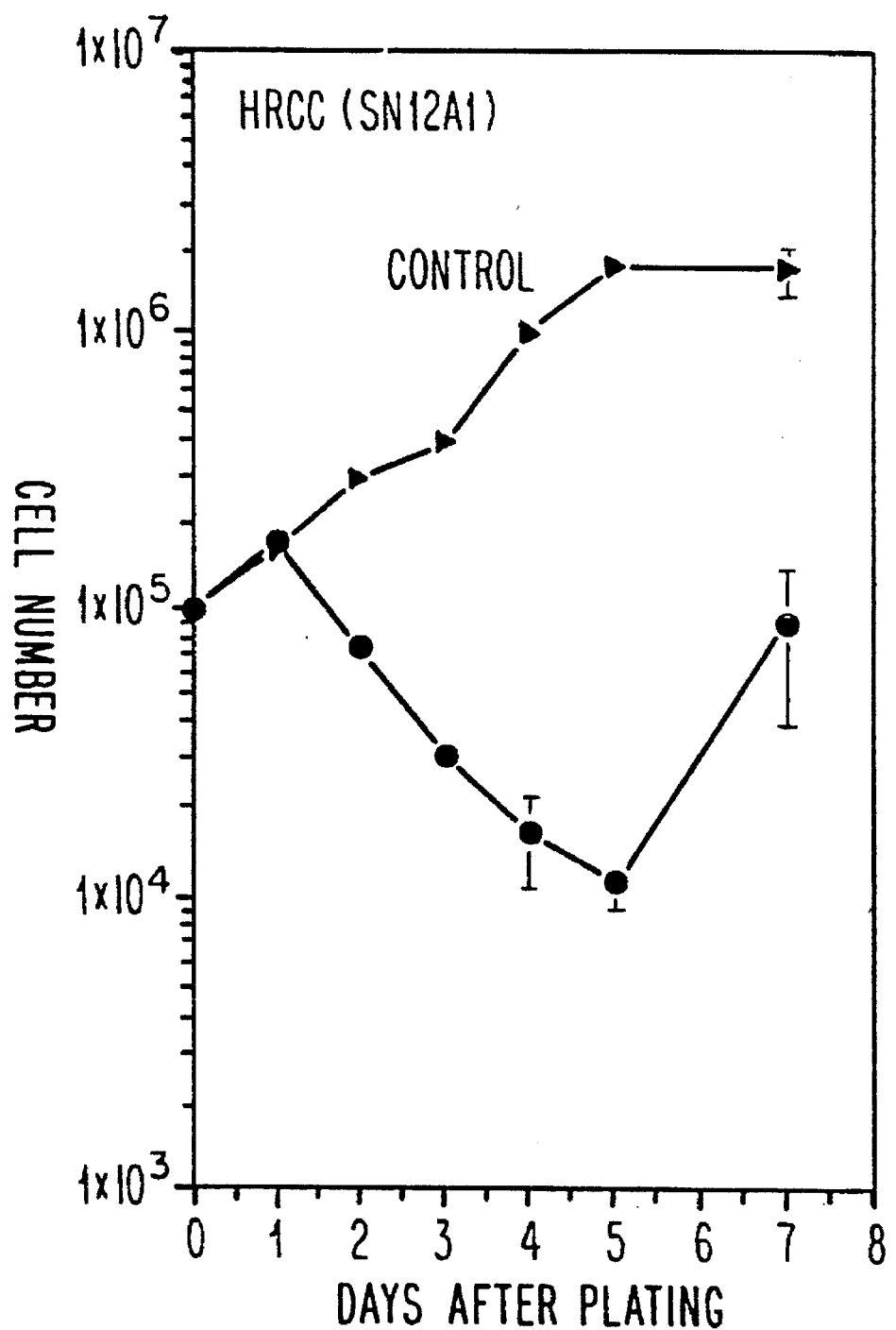
Figure 4:
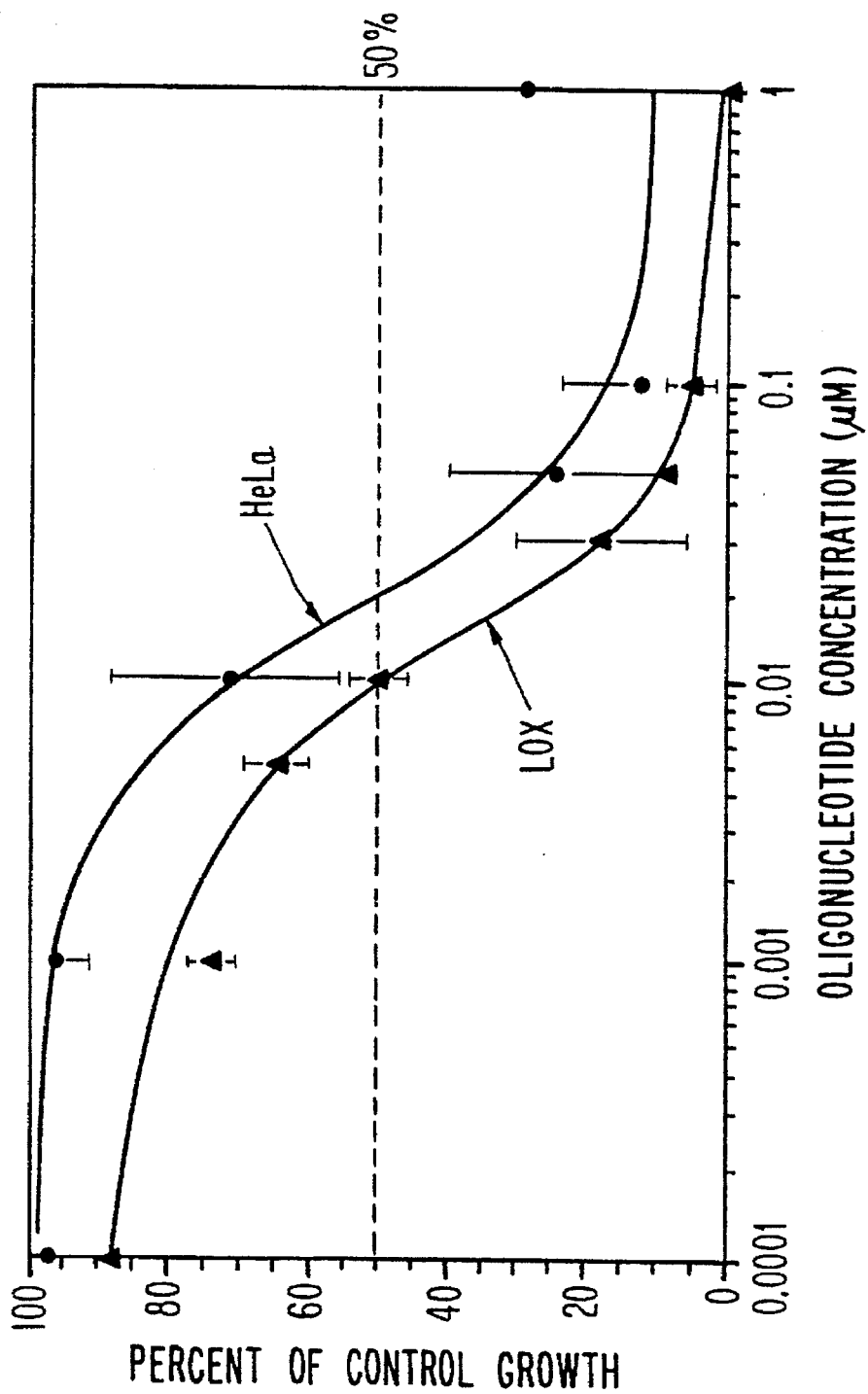
FIG. 4 depicts a dose-response curve of antisense oligonucleotide SEQ ID NO: 9 for HeLa (filled circles) and LOX (filled triangles) cells. The cell counts were converted to percent of control growth and all data from the cell growth control experiments on two days after treatment were plotted against oligonucleotide SEQ ID NO: 9 concentration. Each datum point of the plots contains 3–9 experiments.

In a second set of experiments, the effect of oligonucleotide SEQ ID NO: 9 was analyzed on LOX (FIG. 3A) and HRCC-SN12A1 (FIG. 3B) cells. In this comparative study, two days after treatment, oligonucleotide SEQ ID NO: 9 produced a 1.2 and 0.7 log cell kill on LOX and SN12A1 cells respectively. The maximum cytocidal effect (1.3 log cell kill) on SN12A1 cells was at 4 days after treatment. All cell types recovered after the treatment nadir (FIG. 3). The relationship of concentration of oligonucleotide SEQ ID NO: 9 to inhibition of cell growth for the HeLa and LOX cells is shown in FIG. 4. The $IC_{50}$ values were 0.02 μM for HeLa cells and 0.01 μM for LOX cells (FIG. 4).

Figure 5A:
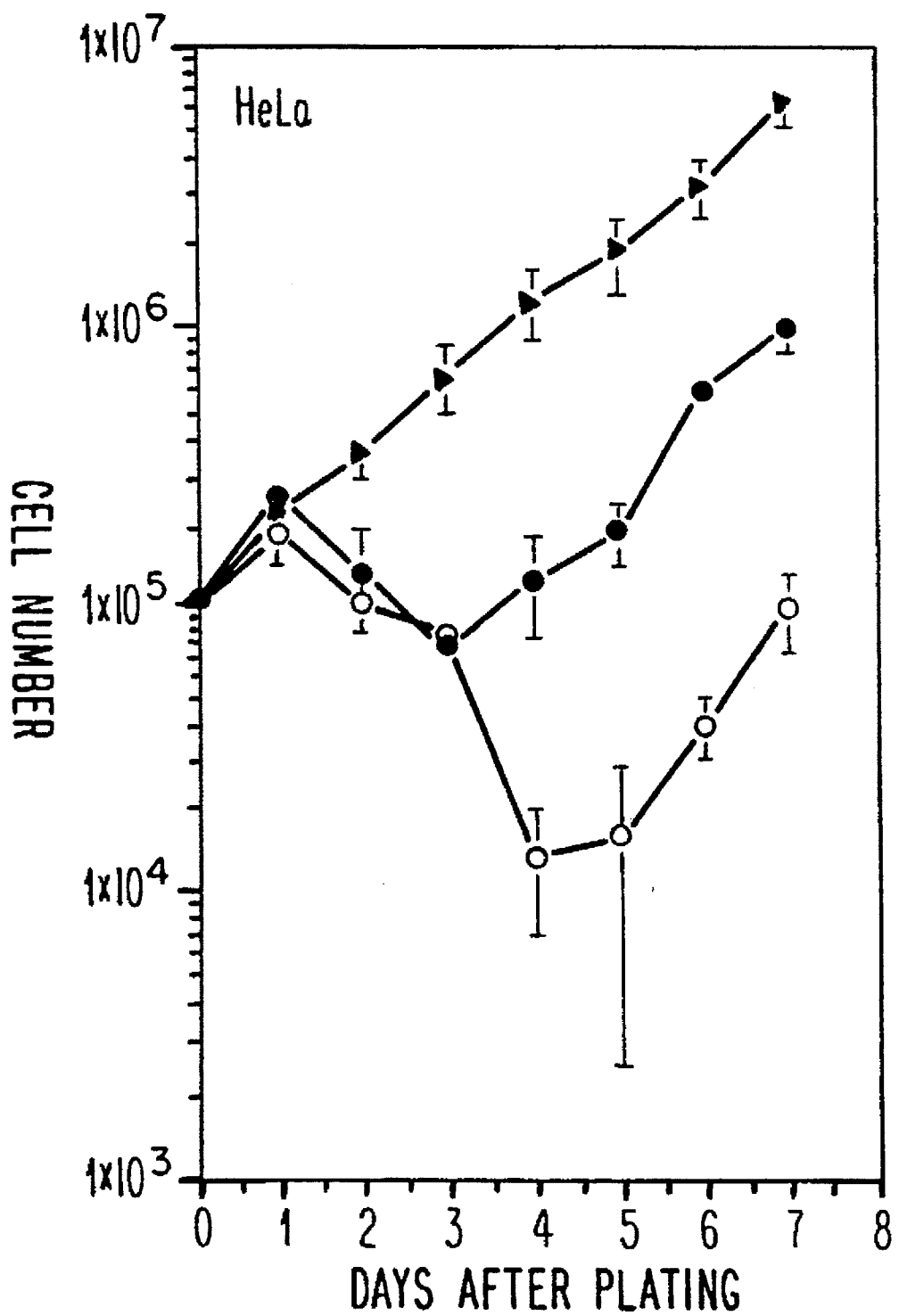
FIG. 5 depicts cell growth inhibitory effect of antisense oligonucleotide SEQ ID NO: 9 on HeLa cells (FIG. 5A) or LOX cells (FIG. 5B). Single treatment (filled circles) was for four hours, 1 day after seeding. Repeated treatment (open circles) was for four hours on days 1 and 3 after seeding. The control (filled triangle) contained DOTMA without oligonucleotide.
Figure 5B:
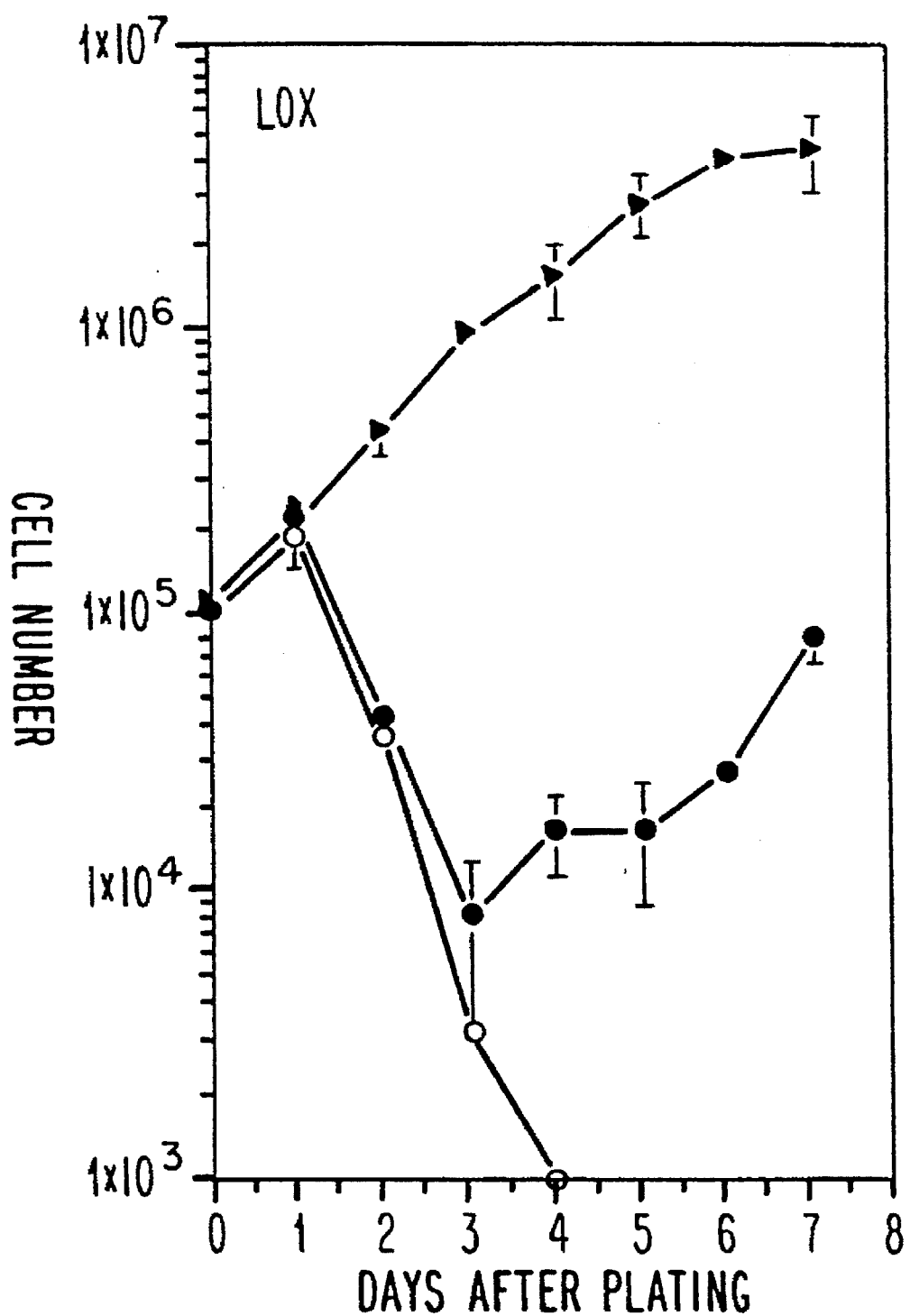

FIG. 5 shows the effect of repeated treatment of antisense oligonucleotide SEQ ID NO: 9 in the presence of DOTMA on HeLa (FIG. 5A) and LOX (FIG. 5B) cells. The cells were treated once for 4 h day 1 after seeding (filled circles) or with two 4 h treatments on days 1 and 3 (open circles). The oligonucleotide concentrations were 0.1 μM for HeLa cells and 0.05 μM for LOX cells. Repeated treatment had additive effects on HeLa cells: after the nadir, the cells recovered. Repeated treatment of LOX cells was more inhibitory than for HeLa cells; a single treatment produced a 1.4 log cell kill of LOX cells. Repeated treatment killed most LOX cells and no recovery was found on day 8.

EXAMPLE 7

Comparison of Oligonucleotides

For analysis of their relative effects on cell growth, oligonucleotide p120 antisense oligodeoxynucleotide-phosphorothioates having sequences as set forth in SEQ ID NO: 2, 3, 4, 5, 6, 7, 9, 10, 11, 12, and 13 were screened using 0.1–0.5 μM oligonucleotide and 10 μg/ml DOTMA in serum-free medium for 4 h. After initial screening (data not shown), the oligonucleotides chosen for further studies had 50% inhibition of cell growth: SEQ ID NO: 2, SEQ ID NO: 5, SEQ ID NO: 6, and SEQ ID NO: 9 (Table 1). The greatest cell growth inhibitory effects (FIG. 1A) were found with oligonucleotides SEQ ID NO: 9 (87.6±11.3%; ±SD, n=22 experiment) and SEQ ID NO: 6 (70.7±24.8%; ±SD, n=12 experiment). The cell growth inhibitory effect of oligonucleotide SEQ ID NO: 9 was significantly greater than that of oligonucleotide SEQ ID NO: 6 (P<0.02).

Figure 6:
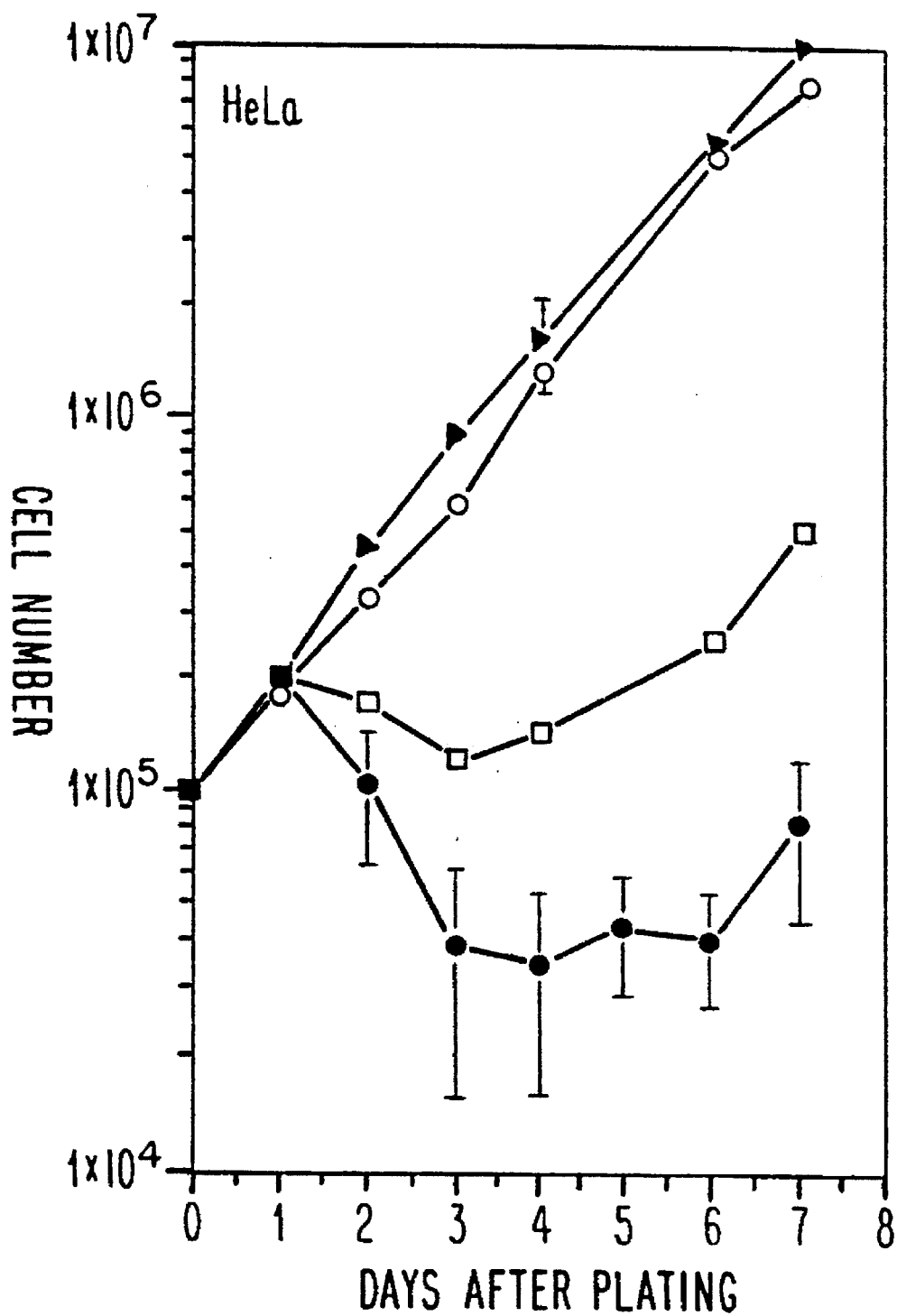
FIG. 6 compares the cell growth inhibitory effect of antisense SEQ ID NO: 9 (closed circles), randomized SEQ ID NO: 15 (having the nucleotide composition of SEQ ID NO: 9, but the sequence is randomized; open squares) and sense SEQ ID NO: 16 (having the complementary sequence to SEQ ID NO: 9; open circles) and a control (closed triangles) containing DOTMA without oligonucleotide on HeLa cells. The cells were treated with oligonucleotide complexed with DOTMA for four hours.

To confirm the specificity of the biological effects of the antisense oligonucleotide SEQ ID NO: 9 on HeLa cells, its effects were compared to a sense oligonucleotide SEQ ID NO: 16 (the sequence of which is complementary to oligonucleotide SEQ ID NO: 9, or the random sequence oligonucleotide SEQ ID NO: 15 (the nucleotide composition is that of oligonucleotide SEQ ID NO: 9; but the sequence was randomized) (Table 1, FIG. 6). A 0.2 log HeLa cell kill was observed with the random sequence SEQ ID NO: 15 compared to a 0.7 log HeLa cell kill with antisense oligonucleotide SEQ ID NO: 9, 2 days after treatment. No inhibitory effect was found with the sense oligonucleotide SEQ ID NO: 16.

EXAMPLE 8

Pharmacology of p120 Antisense Oligonucleotide Phosphorothioates

Phosphorothioate oligonucleotide SEQ ID NO: 9 was labeled with [$\gamma^{32}$P]ATP by T4 polynucleotide kinass to analyze cellular uptake, efflux and stability in the presence or absence of DOTMA. The cellular uptake had a plateau after 1 hour treatment. 5–15 fold more of oligonucleotide SEQ ID NO: 9 was associated with the cells in the presence of DOTMA than in its absence. 60% of the oligonucleotide localized to the nuclei after 4 hours treatment in the presence of DOTMA, approximately 50% remained in the cells 20 hours post-treatment. The stability of phosphorothioate oligonucleotides was much greater than the phosphodiester oligonucleotides. Only 40% degradation of the phosphorothioate oligonucleotide was found after 24 hours in 10% serum-containing medium. More than 50% of the phosphodiester oligonucleotide was degraded within 1 hour. DOTMA enhanced the activity of antisense oligonucleotide phosphorothioate.

EXAMPLE 9

In Vivo Studies in Nude Mice

Intraperitoneally (i.p.) transplanted, exponentially growing LOX ascites tumor cells were harvested from nude mice, washed and resuspended in serum-free RPMI medium. A total of $2\times10^6$ viable cells (determined by trypan blue exclusion) in 0.5 ml RPMI medium were injected i.p. into the homozygous mutant, HSd: Athymic Nude-nu male mice (Sambrook, et al., 1989). Treatment was started 1 day after the i.p. injection of tumor cells and the oligonucleotide in the presence of DOTMA was given i.p. on days 1, 3 and 5. Tumor growth was followed by daily inspection of the animals. The experiments were terminated when the ascite tumors were visible both in controls and treated animals, generally by day 14. All animal experimentation followed the guidelines of the Baylor College of Medicine and New York Academy of Sciences.

EXAMPLE 10

Tumor Growth Inhibition of Oligonucleotide SEQ ID NO: 9 in vivo

Figure 7:
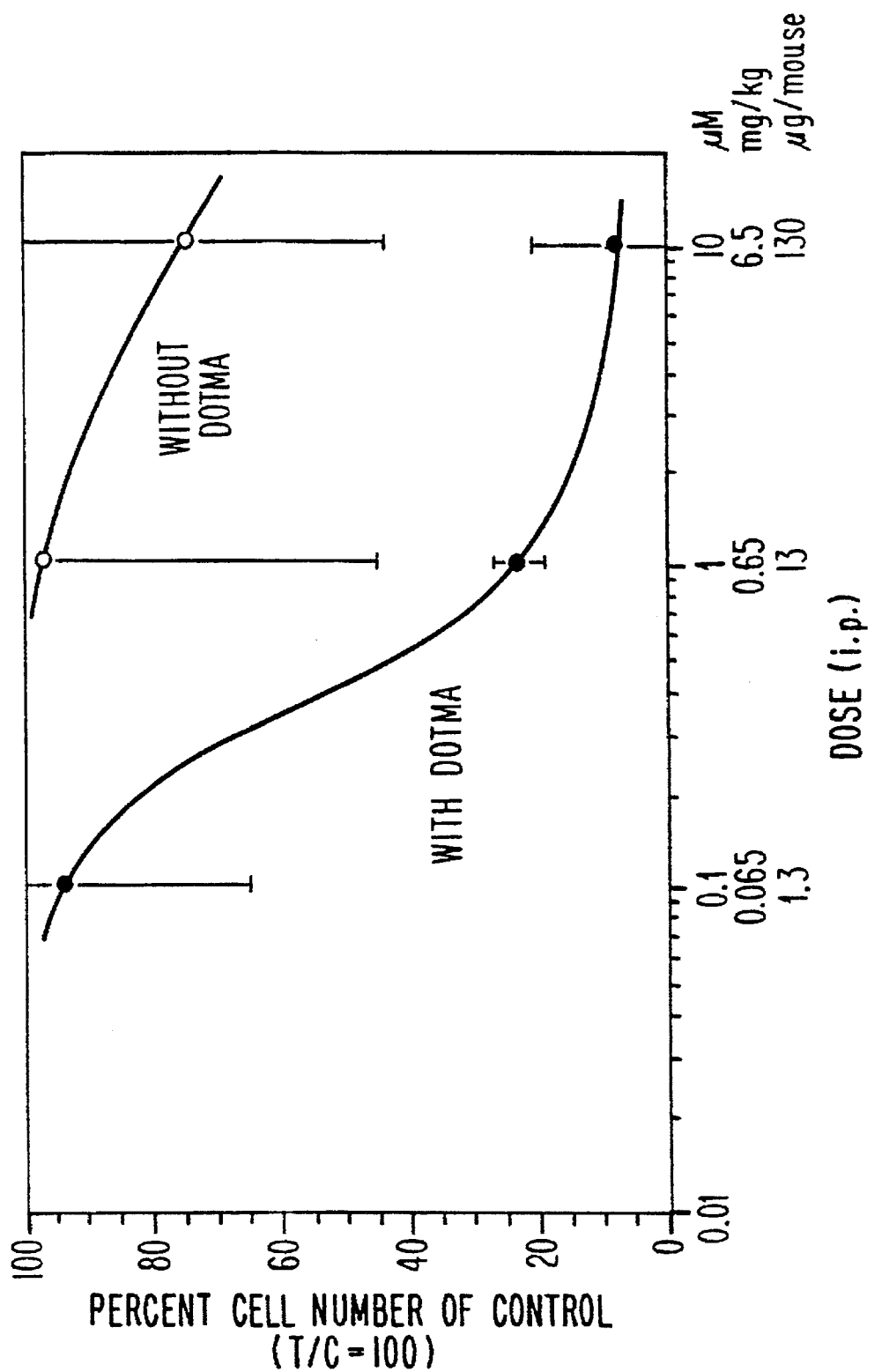
FIG. 7 depicts a dose response curve depicting the tumor growth inhibitory effect of antisense oligonucleotide SEQ ID NO: 9 on human LOX ascites tumor in nude mice. Treatment was on days 1, 3, and 5 with oligonucleotide SEQ ID NO: 9 with DOTMA (filled circles) and without DOTMA (open circles).

The tumor growth inhibitory effect of antisense oligonucleotide SEQ ID NO: 9 was studied on i.p. injected LOX tumor cells. FIG. 7 shows the dose-response curves of treatment on days 1, 3 and 5 with oligonucleotide SEQ ID NO: 9 alone without DOTMA (open circles) or with oligonucleotide SEQ ID NO: 9 complexed with DOTMA (filled circles). No tumor growth inhibition or other toxic effects occurred after treatment with PBS alone or DOTMA in PBS (1–10 mg/kg bodyweight). Oligonucleotide SEQ ID NO: 9 complexed with DOTMA inhibited cell growth in vivo by 80% with the 0.65 mg/kg bodyweight dose and by 90% with 6.5 mg/kg bodyweight; the $IC_{50}$ was 0.26 mg/kg bodyweight.

EXAMPLE 11

Nuclear Aberrations in Human Tumor Cells Following Treatment with Antisense Oligonucleotiae SEQ ID NO: 9

HeLa and LOX human tumor cell lines were analyzed by light and fluorescence microscopy after 4 hours treatment with 0.2 or 0.4 μM antisense (SEQ ID NO: 9) or sense (SEQ ID NO: 16) oligonucleotide with DOTMA. Staining with methylene blue (RNA), anti-p120 monoclonal antibody (p120), or Hoeschst dye 33258 (DNA) showed mitotic cells decreased by 50% at 4 hours and 70% at 8 to 72 hours post-treatment. Nucleolar unraveling and fragmentation and chromatin alterations were observed. In some LOX cells chromatin was condensed as in prophase arrest. In HeLa cells, chromatin was condensed and compacted. Decreased mitoses correlated with decreased $^3$H-thymidine incorporation. Cell growth decreased 70–80%.

---

What is claimed is:

1. An antisense oligonucleotide having the sequence 5'-CACCCGCCTT GGCCTCCCAC-3' (SEQ ID NO: 9).

2. An antisense oligonucleotide having the sequence 5'-CACCCGCCTT GGCCTCCCAG-3' (SEQ ID NO: 14).

3. The antisense oligonucleotide of claim 1 wherein at least one of the linking groups between nucleotides is a phosphorothioate moiety.

4. The antisense oligonucleotide of claim 2 wherein at least one of the linking groups between nucleotides is a phosphorothioate moiety.

* * * * *